US004001686B2

United States Statutory Invention Registration [19]

[11] Reg. Number: H1686

[45] Published: Oct. 7, 1997

Scott et al.

[54] PROCESS FOR REMOVING PEROXIDE IMPURITIES FROM ACRYLONITRILE MONOMERS

[75] Inventors: Charles E. Scott, El Lago; David S. Hagen, Houston, both of Tex.

[73] Assignee: Sterling Chemicals, Inc., Houston, Tex.

[21] Appl. No.: 673,913

[22] Filed: Jul. 1, 1996

[51] Int. Cl.[6] ..... C07C 255/00

[52] U.S. Cl. ..... 558/388

[58] Field of Search ..... 558/333

[56] References Cited

PUBLICATIONS

*Confidential, internal document*; Analytical procedure for determining peroxides in acrylonitrile; Robert A. Fischer, Sterling Chemicals, Inc. (Apr. 15, 1993).

Draft #7, Analytical method for determining peroxides in acrylonitrile, ASTM E–1784–96 (Oct. 1995).

Product information sheet for *Selexsorb CD*; Alcoa Industrial Chemicals Division (Jun. 1991).

*Primary Examiner*—Charles T. Jordan
*Assistant Examiner*—Meena Chelliah
*Attorney, Agent, or Firm*—Jenkens & Gilchrist, P.C.

[57] ABSTRACT

A process is provided for removing peroxide contamination from acrylonitrile. The process includes contacting the acrylonitrile with an activated alumina adsorbent and separating the acrylonitrile product from the alumina. The contaminated acrylonitrile is contacted with the activated alumina adsorbent for a time sufficient for the peroxide contaminate to be adsorbed by the activated alumina. The activated alumina may also be used to selectively remove color promoting contaminates in an acrylonitrile product.

3 Claims, No Drawings

PROCESS FOR REMOVING PEROXIDE IMPURITIES FROM ACRYLONITRILE MONOMERS

BACKGROUND

1. Field of the Invention

This invention is a process for removing peroxide impurities from acrylonitrile monomer by contacting the monomer with an activated alumina adsorbent.

2. Background of the Invention

Periodically, during the production of acrylonitrile monomer the product produced is so contaminated with an impurity characterized as a peroxide that it exceeds tolerable specifications and becomes unmarketable. It must be treated to reduce the quantity of the peroxide present in order to avoid loss. Even though the impurity is characterized as peroxide, the precise chemical definition is unknown but, it yields a peroxide indicator when tested using an iodide colorimetric test. The normal specification for acrylonitrile relating to the peroxide presence is less than 0.2 parts per million by weight (expressed as hydrogen peroxide). This means that organic and aqueous peroxides as well as nitrites could give a positive result. Because peroxides are usually relatively unstable, it is very difficult to analyze with specificity the specific peroxides present. Accordingly, it makes process changes to alleviate peroxide formation very difficult, leaving purification either to peroxide destruction or removal.

One attempt to reduce peroxide contamination of acrylonitrile involved recycling contaminated product through the recovery system of the process which becomes very costly in terms of adding processing costs to the product. Another attempt involved circulating acrylonitrile high in peroxides through storage tanks and depended upon extraneous iron oxide rust, or other oxides, in the tanks and the piping to be picked up and destroy the peroxide. This process is relatively unpredictable since the amount of circulation necessary is unknown and the precision at which the peroxide level can be tested at these low levels has a wide margin for error, almost 0.05 ppm by weight. It accordingly is an object of this invention to purify acrylonitrile from contaminating peroxides through a simple removal process. It is a further objective of this invention to remove peroxide contamination from acrylonitrile without simultaneously removing water and inhibitor packages from the acrylonitrile.

SUMMARY OF THE INVENTION

Surprisingly, it has been discovered that acrylonitrile contaminated with peroxides, whether containing water or p-methoxyphenol inhibitors can be brought into contact with an activated alumina adsorbent for a period of time sufficient to remove such peroxide contaminates onto the alumina, followed by separation of the acrylonitrile produces an acrylonitrile product within specification (less than 0.2 ppm by weight peroxide, expressed as $H_2O_2$) without harming the inhibitor package or unduly drying the product. The presence of the inhibitor package, whether a combination of p-methoxyphenol and water or some other inhibitor, prevents the premature polymerization of the acrylonitrile. The presence of the water and the p-methoxyphenol is important from a regulation point of view, as well as for technical reasons, since uninhibited acrylonitrile cannot be shipped through a common carrier and this inhibitor combination is popular and effective in the inhibiting amounts of from 0.25 to about 0.5 weight percent water and from 35 to about 50 parts per million by weight of the preferred p-methoxyphenol.

The adsorbent used is an activated alumina having a surface area of from about 150 to about 400 square meters per gram. Activated alumina is a popular adsorbent and is sold and promoted as an adsorbent for many materials including water, ether and peroxides generally. However, surprisingly, in the practice of this process, contact with alumina for a period of time from about 0.5 to about 2.5 minutes, preferably, from about 1.0 to about 2.0 minutes removes the peroxide but leaves the water and ether.

DETAILED DESCRIPTION OF THE INVENTION

In the practice of this invention acrylonitrile containing peroxide contamination is brought into contact with an activated alumina adsorbent for a time period sufficient for the peroxide contaminant to be adsorbed by the activated alumina to produce an acrylonitrile product having less than about 0.2 part per million by weight peroxides. In the practice of this invention it will be understood that the term "peroxide" is meant to include those contaminants which can be quantified by the classic iodide colorimetric testing procedure. A standard procedure for this test has been recently established as ASTM Test No. E-1784-96.

The acrylonitrile, whether in crude form (containing high concentrations of water, acetic acid and/or cyanide) or as final product (comprising 99.5 weight percent or more acrylonitrile, the inhibitor package and residual amounts of other chemicals) from the output of the purification section or from storage tank, from time to time is found to have 0.6 to 0.8 part per million by weight of peroxides, sometimes reaching as high as 1.5 to 2 parts per million or even more peroxide contamination. This greatly exceeds the specification for saleable product and is undesirable because the presence of the peroxides may cause the acrylonitrile to prematurely polymerize.

The activated alumina used is preferably in a spherical configuration having a diameter from about 2 millimeters to about 5 millimeters and a surface area from about 190 square meters per gram to about 420 square meters per gram. While different sized alumina may be used, it is preferable that the alumina contacted by the acrylonitrile contaminated with peroxides be a uniform size. Normally the alumina will be placed in one or more beds in a packed column as is well known to those skilled in the art. The flow of the contaminated acrylonitrile may be in any direction, either up or down for a vertical flow bed. However, it is possible to use a horizontal flow bed and pump through the bed as in a pipeline. The preferred direction is to flow the acrylonitrile up through the bed of activated alumina which assures a more uniform coverage. The residence time of contact between the acrylonitrile and the activated alumina will be from about 30 seconds to about 2.5 minutes, preferably from about one to two minutes. Of course the time of contact will vary according to the amount of peroxide contamination in the acrylonitrile. When there are low levels of contamination, the contact time may be shorter and vice versa. The reactor design is well within the skill of a process engineer using standard engineering principles based upon the desired residence time. The preference is to design the system for at least about a 1½ minute residence time and then adjust either the flow rate or diameter of the reactor vessel containing activated alumina adsorbent to achieve the desired residence time. While many adsorbents are satisfactory for the practice of this invention and may be determined through running a simple test as described below, the preferred is the alumina product marketed under the trademark, "SELEXSORB CD," by Alcoa Industrial Chemicals Division of Vidalia, La.

The size of the reactor can be determined by using common engineering techniques, such as the linear hourly space velocity and residence time desired using expedients such as the known output rate of the pump which will feed the material to the bed.

For completeness sake, in the production of acrylonitrile which is to be sold without further processing or storage, it may be a preferred process step to filter the acrylonitrile coming out of the activated alumina bed using one of commonly known filters, with a 50–60 micron filter being satisfactory. Of course, in accordance with customary engineering principles, a pair of parallel beds may be used to allow operation of one bed while the other, having experienced breakthrough of peroxides, is being repacked. Further, in the case of a severe contamination of the feed with peroxide, the two beds could be used in series to provide a longer residence time.

The pressure at which the operation is practiced is not believed to be critical. Any pressure which accomplishes the desired flow rate and residence time while maintaining the acrylonitrile in the liquid phase should be satisfactory. Ambient temperatures may be used in the practice of the invention with the acrylonitrile contacting the activated alumina at the same temperature as it is prior to contact. This may be ambient temperature (as when the acrylonitrile to be treated is from a storage tank) or some higher temperature (as when crude acrylonitrile is processed prior to distillation, or when the distilled product is treated prior to shipment). A treatment temperature from about 15° C. to about 40° C. is preferred.

The foregoing discussion of the practice of this invention will be further demonstrated by the following examples which are offered for purposes of illustration and not limitation of the invention described.

EXAMPLE 1

An experimental reactor was built approximately 5 feet high with ½ vertical tubing with a reservoir on top. The 'reactor' was a 9" section of ½" tubing filled with ⅛" activated alumina balls ("SELEXSORB" CD from Alcoa) at the bottom of this tubing run held in place with wire mesh. 5 quarts of acrylonitrile with 1.3 ppm of $H_2O_2$ were gravity fed through the reactor. The product of the reactor was found to have 0.089 ppm of peroxides, well within spec. The parameters calculated from the test reactor were:

1) LHSV: 31 ft/hr
2) Residence time: 87 second (Note: this is an apparent residence time)
3) Loading: 1552 lb/hr/ft$^2$ Even though dusting of the alumina was anticipated to be a concern, no dusting was observed.

EXAMPLE 2

The test of example 1 was repeated, first using 100 cc of acrylonitrile. The table shows that very little, if any, water was removed but the peroxides did disappear.

| Component | ABV. | Treated AN After 100 cc | Treated AN After 2000 cc | AN Feed Concentration |
|---|---|---|---|---|
| p-Methoxyphenol | MEHQ | 37.6 ppm | 37.2 ppm | 40 ppm |
| Water | $H_2O$ | 0.357 wt % | 0.36 wt % | 0.40% wt % |
| Hydrogen Cyanide | HCN | 0.1 ppm | 0.4 ppm | 1 ppm |
| 'Peroxide' | | 0.001 ppm | 0.089 ppm | 1.3 ppm |
| Acetic Acid | HoAc | 1.1 ppm | 1.3 ppm | <1 ppm |
| pH | | 7.0 | 6.9 | 6.93 |

After 2000 cc of contaminated acrylonitrile feed was passed through the bed, the peroxide level began to increase, indicating a breakthrough in the bed. The stabilizing system, comprised of water and the p-methoxyphenol inhibitor, was only very slightly affected by the treatment surprisingly indicating that the peroxide could be removed while water and an ether were not.

EXAMPLE 3

Alumina reactor beds were designed for 50 seconds of residence time to test a large quantity (400–600 gpm) of acrylonitrile contaminated with 1–2 ppm of peroxide. The reactors were manufactured from two 30 inch internal diameter pipes, 5 feet long which were oriented vertically and packed with activated alumina. The reactors were run in series with upward flow of the acrylonitrile. Flow came into the reactor via a 6 inch connection on the bottom and out a 6 inch connection on the top. Screens were used to keep the alumina in place. Both ⅛" and ¼" alumina balls ("SELEXSORB" CD) were tried. The best results came when the whole of the reactor was filled with ⅛" balls. Each reactor was filled within 6 inches of the top.

Dusting of the alumina was anticipated to be a possible problem so 50–60 micron filters were added after the reactors. Dusting could be mostly avoided by flushing the alumina with water before starting.

Treated acrylonitrile having less than 0.2 ppm of peroxide was successfully obtained both with a crude acrylonitrile feed (containing 80 to 95 weight percent acrylonitrile, 0 to 12 weight percent hydrogen cyanide, 0 to 8 weight percent water, and traces of other chemicals), and with a finished, but peroxide contaminated, acrylonitrile feed (in excess of 99.0% acrylonitrile).

The foregoing invention having been described and illustrated through the examples can readily be understood by those skilled in the art. Many modifications and changes may be made without departing from the scope of such invention as set forth in the claims appended hereto.

We claim:

1. A process for removing peroxide contamination from acrylonitrile which comprises contacting the acrylonitrile with an activated alumina adsorbent for a time sufficient for the peroxide contaminate to be adsorbed by the activated alumina and to produce an acrylonitrile product having less than about 0.2 ppm peroxide, and separating the acrylonitrile product from the alumina.

2. A process for treating a material comprising acrylonitrile and minor amounts of color promoting contaminants, which process comprises contacting said material with alumina so as to selectively remove said color promoting contaminants and produce an acrylonitrile product having a reduced content of said contaminants.

3. A process for treating a material consisting essentially of not less than 99 weight percent acrylonitrile, between about 0.25 and about 0.5 weight percent of a color stabilizing system comprising water and p-methoxyphenol, and greater than 0.5 ppm of color promoting contaminants, which process comprises contacting said material with an adsorbent comprising activated alumina having a surface area of between about 150 and about 400 square meters per gram at a temperature no greater than 75° C. with a contacting time of between about 0.5 and about 2.0 minutes so as to selectively adsorb said color promoting contaminants and produce an acrylonitrile product having less than about 0.2 ppm of said contaminants but not less than 85 percent of the concentration of said color stabilizing system in said material.

* * * * *